(12) United States Patent
Kitamura et al.

(10) Patent No.: US 8,398,937 B2
(45) Date of Patent: Mar. 19, 2013

(54) MICROCHANNEL AND ANALYZING DEVICE

(75) Inventors: Shigeru Kitamura, Kyoto (JP); Kotaro Shinozaki, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 158 days.

(21) Appl. No.: 12/988,602

(22) PCT Filed: Mar. 30, 2009

(86) PCT No.: PCT/JP2009/056503
§ 371 (c)(1),
(2), (4) Date: Oct. 19, 2010

(87) PCT Pub. No.: WO2009/130976
PCT Pub. Date: Oct. 29, 2009

(65) Prior Publication Data
US 2011/0038766 A1  Feb. 17, 2011

(30) Foreign Application Priority Data
Apr. 25, 2008  (JP) ................. 2008-115481

(51) Int. Cl.
*B01L 3/00* (2006.01)
*F15D 1/00* (2006.01)

(52) U.S. Cl. ........ 422/504; 422/502; 422/506; 422/507; 137/391; 137/561 R

(58) Field of Classification Search .............. None
See application file for complete search history.

(56) References Cited

U.S. PATENT DOCUMENTS

| | | | |
|---|---|---|---|
| 4,756,884 A | 7/1988 | Hillman et al. | |
| 7,754,151 B2 | 7/2010 | Kitawaki et al. | |
| 2005/0118070 A1 | 6/2005 | Griss et al. | |
| 2006/0008381 A1 | 1/2006 | Taguchi et al. | |
| 2009/0031829 A1 | 2/2009 | Matsumoto | |
| 2009/0220948 A1* | 9/2009 | Oviso et al. .............. | 435/6 |

FOREIGN PATENT DOCUMENTS

| | | |
|---|---|---|
| JP | 6-94724 | 4/1994 |
| JP | 2004-150804 | 5/2004 |
| JP | 2005-181295 | 7/2005 |
| WO | WO 2006/098370 | 9/2006 |
| WO | WO2006098696 * | 9/2006 |
| WO | WO 2006/106608 | 10/2006 |
| WO | WO 2007/013562 | 2/2007 |

* cited by examiner

*Primary Examiner* — In Suk Bullock
*Assistant Examiner* — Timothy G Kingan
(74) *Attorney, Agent, or Firm* — Fox Rothschild LLP

(57) ABSTRACT

A microchannel 4 for transporting a specimen S using capillary phenomenon includes an analysis chamber 6 having a cross-sectional area larger than those of portions located in front of and behind the analysis chamber 6 in the direction of flow, an inflow opening 5 through which the specimen S flows into the analysis chamber 6, and a discharge portion 7 through which the specimen S is discharged from the analysis chamber 6. The discharge portion 7 includes a pair of discharge openings 71a and 71b located opposite to each other with respect to the inflow opening 5. With this structure, impairment of transport of the specimen S due to the presence of a residual air bubble is avoided.

7 Claims, 13 Drawing Sheets

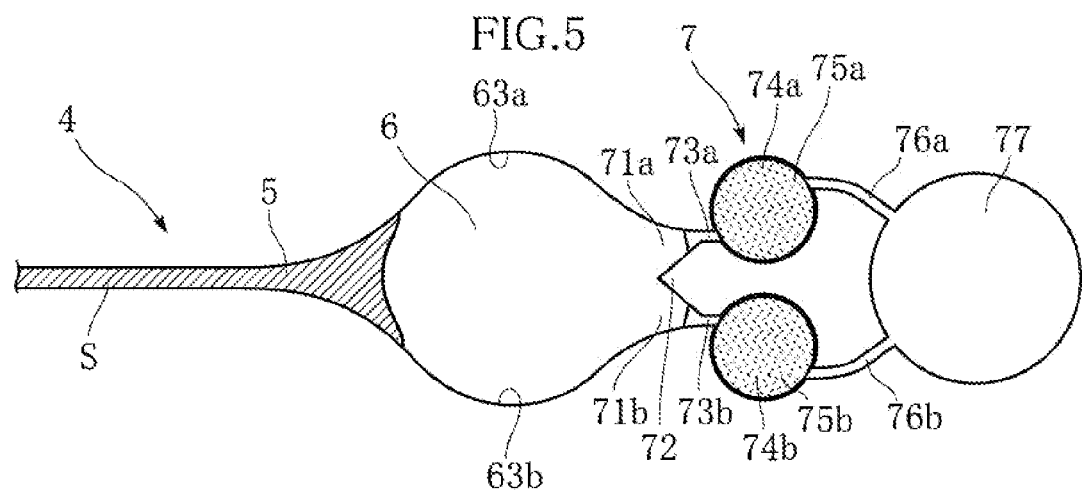
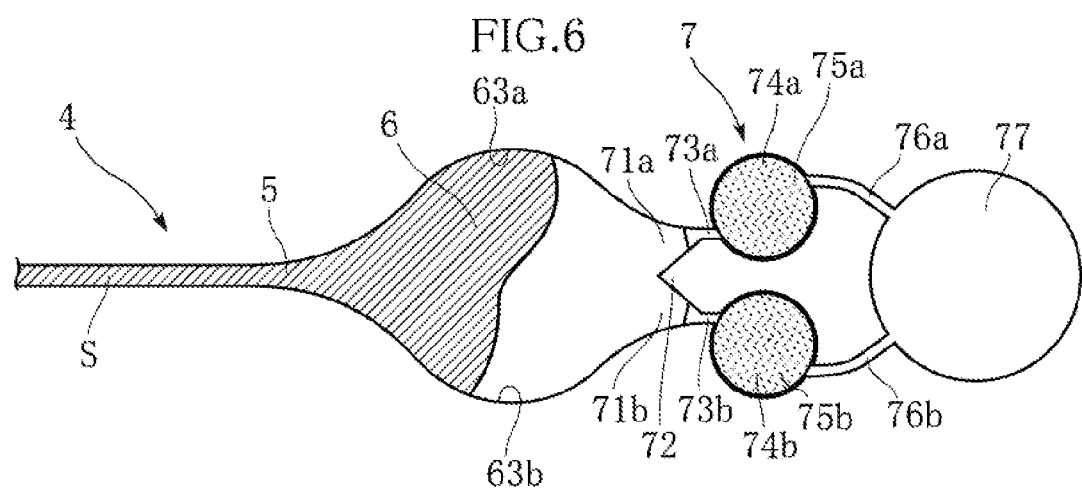
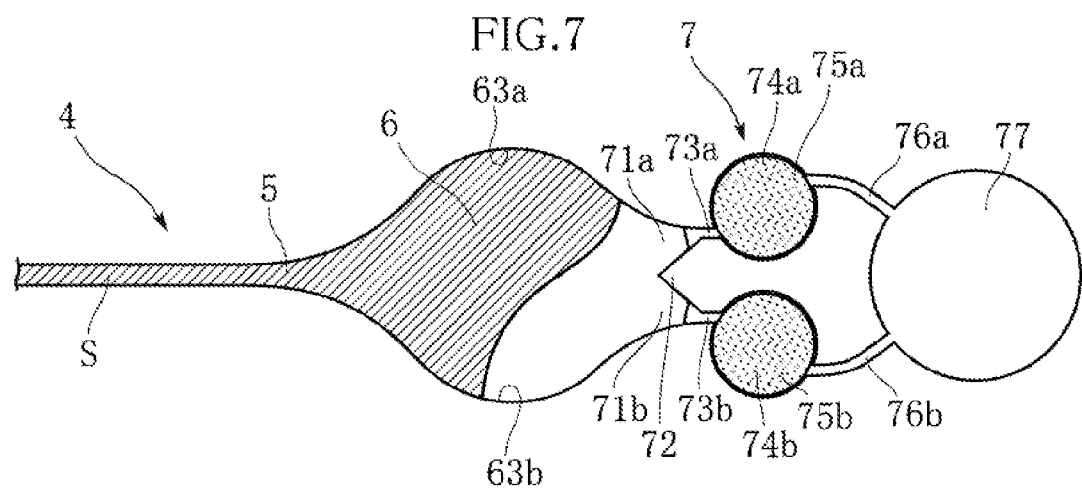

MICROCHANNEL AND ANALYZING DEVICE

TECHNICAL FIELD

The present invention relates to a microchannel for transporting a liquid and an analyzing device.

BACKGROUND ART

Reaction liquids obtained when a specimen and a reagent are allowed to react, for example, have been conventionally analyzed by methods using optical techniques. In the case of analyzing a specimen using such methods, an analyzing device is used that provides a reaction field. In the case of analyzing minute amounts of specimens, analyzing devices are used in which a microchannel is formed for transporting a liquid using capillary phenomenon (see, for example, Patent Document 1).

FIG. 17 shows an example of such a microchannel. The microchannel X shown in the figure includes an inflow opening 91, an analysis chamber 92, a discharge opening 93 and an open chamber 94, and is configured to allow a specimen S such as blood to be transported by capillary phenomenon. The analysis chamber 92 has a circular cross-section, and optically analyzes the concentration of a specific component in the specimen, for example, by allowing light to pass therethrough when filled with the specimen. The analysis chamber 92 is defined by a pair of mutually opposing side surfaces 92$a$ and 92$b$, and a pair of surfaces (not shown) that are perpendicular to the side surfaces 92$a$ and 92$b$ and mutually opposed with a slight distance there between. The open chamber 94 is connected to the analysis chamber 92 via the discharge opening 93. The open chamber 94 is open to the atmosphere by a pathway not shown.

Liquid is transported through the microchannel X in the following manner. First, a specimen S such as blood is introduced into the upstream side of the microchannel X. This specimen S is introduced by capillary phenomenon, and flows into the analysis chamber 92 from the inflow opening 91 as shown in FIG. 18. The vicinities of the side surfaces 92$a$ and 92$b$ constitute regions that are surrounded on three sides by the pair of surfaces and the side surface 92$a$ or the pair of surfaces and the side surface 92$b$, and facilitate the action of capillary force on the specimen S to increase thrust. Consequently, the specimen S tends to proceed along the side surfaces 92$a$ and 92$b$.

However, it is difficult to make the side surfaces 92$a$ and 92$b$ to be completely identical. For example, microscopic variations in shape attributable to the degree of processing accuracy during manufacturing cannot be avoided at the boundaries between the side surfaces 92$a$ and 92$b$ and the pair of surfaces. Alternatively, capillary force varies considerably if oil and the like adhere to the side surfaces 92$a$ and 92$b$. In such circumstances, a considerable difference occurs between the speed at which the specimen S proceeds along the side surface 92$a$ and the speed at which the specimen S proceeds along the side surface 92$b$. If this happens, the specimen S unevenly proceeds along the side surface 92$a$, for example, as shown in FIG. 19. As a result, the specimen S reaches the discharge opening 93 by passing over only the side surface 92$a$ as shown in FIG. 20, thereby causing the discharge opening 93 to be blocked by the specimen S. As a result, an air bubble B1 ends up forming in the vicinity of the side surface 92$b$. Once this happens, even if analysis is carried out by an optical technique, light radiated onto the analysis chamber 92 ends up passing through the air bubble B1 in addition to the specimen S. Thus, it becomes no longer possible to properly analyze a specific component of the specimen S.

Patent Document 1: JP-A-2004-150804

DISCLOSURE OF THE INVENTION

Problems to be Solved by the Invention

An object of the present invention, which is conceived under the above-described circumstances, is to provide a microchannel and an analyzing device that are able to properly transport a liquid.

Means for Solving the Problems

According to a first aspect of the present invention, there is provided a microchannel for transporting a liquid. The microchannel includes: an inflow portion located on the upstream side in the direction of flow; a discharge portion located on the downstream side in the direction of flow; and an enlarged portion located between the inflow portion and the discharge portion and having a cross-sectional area larger than those of the inflow portion and the discharge portion. The discharge portion includes a pair of discharge openings located opposite to each other with respect to the inflow portion as viewed in the direction of flow.

In a preferred embodiment of the present invention, the liquid is transported using capillary phenomenon.

In a preferred embodiment of the present invention, the discharge portion further includes a separating portion located between the pair of discharge openings and tapered towards the upstream side in the direction of flow.

In a preferred embodiment of the present invention, the discharge portion further includes a retaining portion that is connected to at least one of the discharge openings on the downstream side in the direction of flow and has a cross-sectional area larger than the discharge opening.

In a preferred embodiment of the present invention, the retaining portion is provided with a swelling member that inhibits the outflow of the liquid from the retaining portion to the downstream side by swelling upon absorbing the liquid.

In a preferred embodiment of the present invention, the retaining portion has a top surface and a bottom surface that face each other with a space therebetween in a direction perpendicular to the direction of flow. The bottom surface includes an island portion located near the center when viewed in the direction in which the top surface and the bottom surface face each other with a space therebetween, and a surrounding portion that surrounds the island portion when viewed in the direction in which the top surface and the bottom surface face each other with a space therebetween, and is farther away from the top surface than the island portion is.

The retaining portion may include a hydrophobic region.

In a preferred embodiment of the present invention, the microchannel further includes: an additional enlarged portion located on the downstream side of the retaining portion in the direction of flow; an additional inflow portion for guiding the liquid from the retaining portion to the additional enlarged portion; and an additional discharge portion into which the liquid from the additional enlarged portion is discharged and includes a pair of additional discharge openings located opposite to each other with respect to the additional inflow portion as viewed in the direction of flow.

In a preferred embodiment of the present invention, an open chamber that can be open to the atmosphere is provided between the retaining portion and the additional inflow portion.

In a preferred embodiment of the present invention, the open chamber is connected to a pressure reducer capable of reducing pressure within the open chamber.

An analyzing device provided according to a second aspect of the present invention includes the microchannel as set forth in the first aspect of the present invention. In the analyzing device, the enlarged portion is used as an analysis field.

Other features and advantages of the present invention will be made clearer from the following detailed description provided with reference to the attached drawings.

BRIEF DESCRIPTION OF THE DRAWINGS

FIG. 5 is a plan view of principal parts depicting liquid transport in the microchannel shown in FIG. 3;

FIG. 6 is a plan view of principal parts depicting liquid transport in the microchannel shown in FIG. 3;

FIG. 7 is a plan view of principal parts depicting liquid transport in the microchannel shown in FIG. 3;

BEST MODE FOR CARRYING OUT THE INVENTION

Preferred embodiments of the present invention are described below with reference to the drawings.

Figure 1:
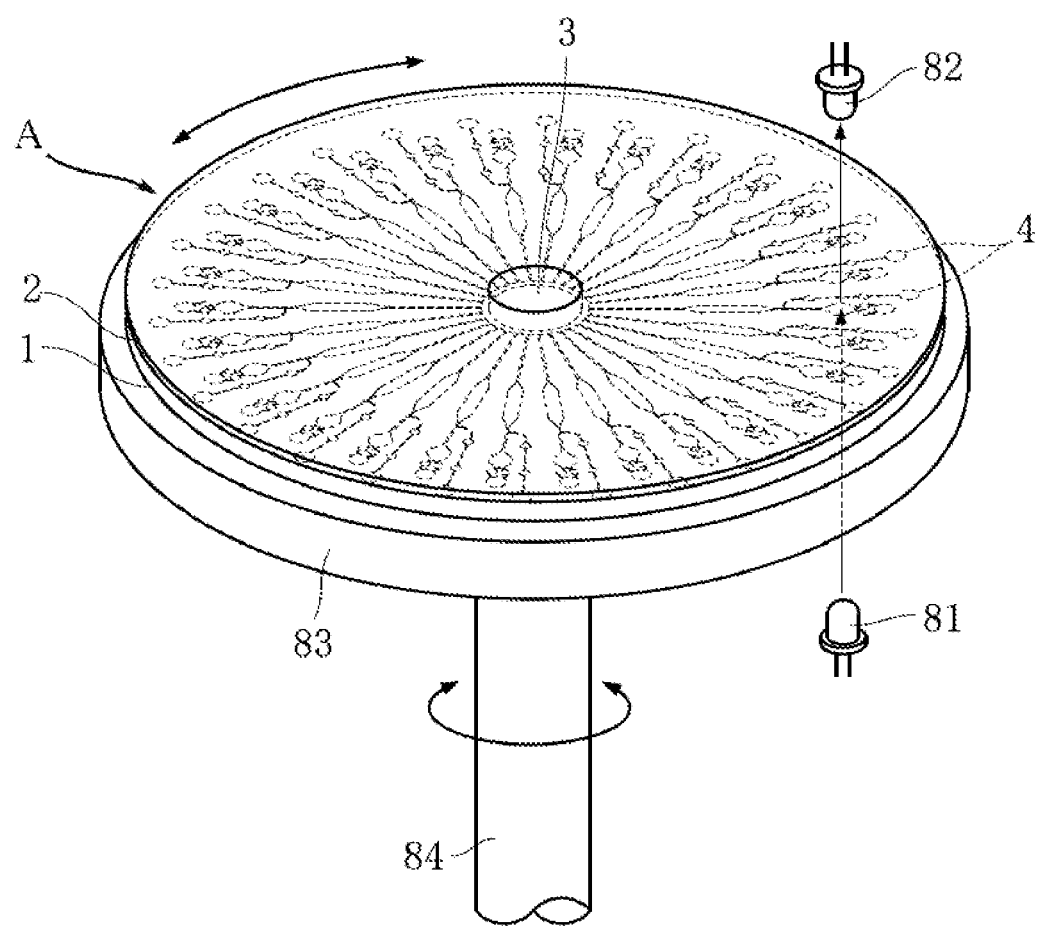
FIG. 1 is a perspective view showing an example of an analyzing device according to the present invention.
Figure 2:
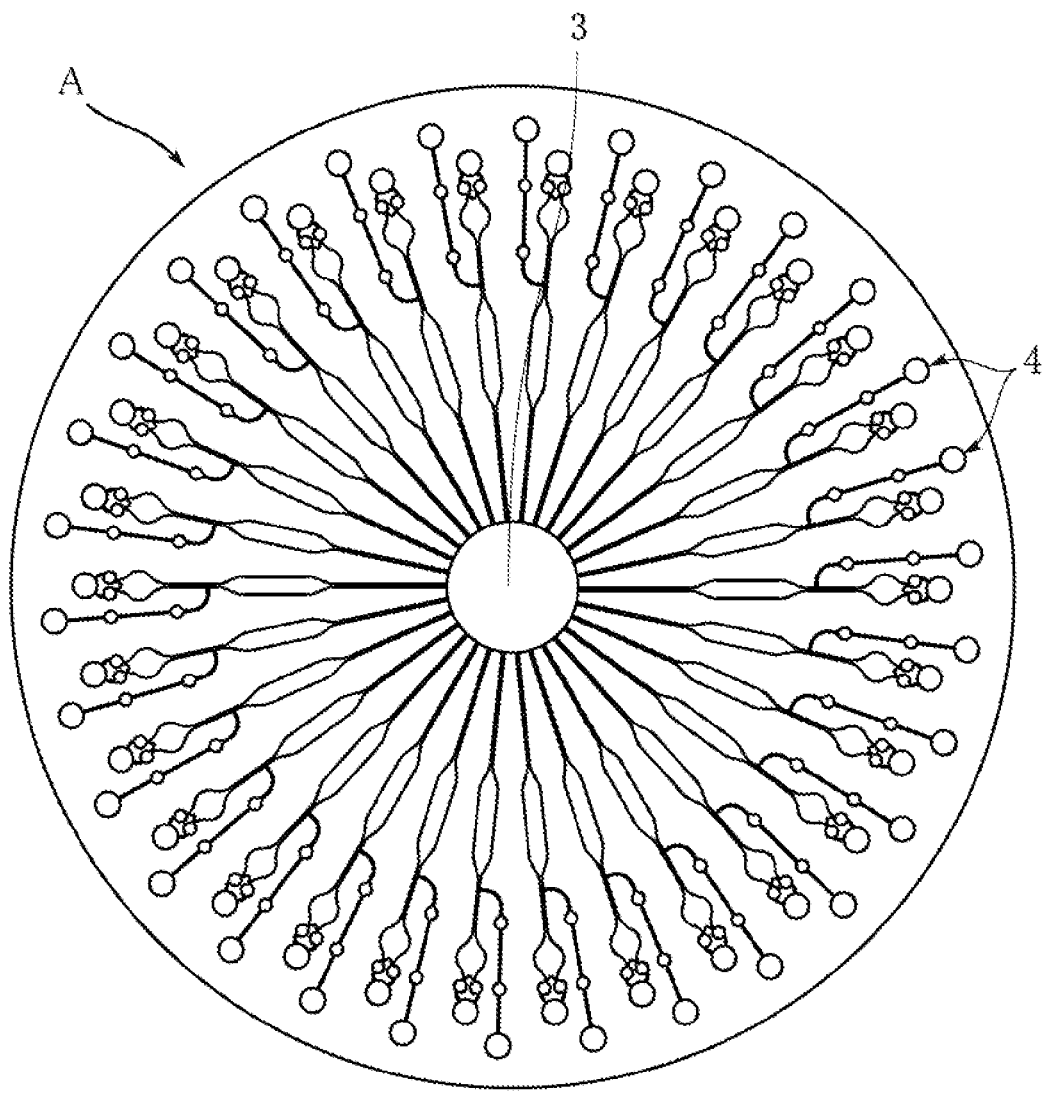
FIG. 2 is a plan view showing the principal parts of the analyzing device shown in FIG. 1.

FIGS. 1 and 2 show an example of an analyzing device according to the present invention. An analyzing device A of the present embodiment is for carrying out analyses relating to a specific component by an optical technique on a specimen S such as blood. The analyzing device A is configured to be installed in an analyzer (not shown). In FIG. 2, a cover 2 to be described later is omitted to facilitate understanding. The analyzing device A is supported by a support stand 83 provided in the analyzer. A rotating shaft 84 is connected to the support stand 83, making the analyzing device A rotatable. A light emitting module 81, which includes an LED chip, for example, serves as a light source that emits light for optical analyses. A light receiving module 82, which includes an silicon photodiode, for example, receives light from the light emitting module 81 that has passed through the analyzing device A. The analyzer is configured to analyze a specific component of the specimen S according to the light receiving state of the light receiving module 82.

The analyzing device A is roughly in the shape of a disc overall. As shown in FIG. 1, the analyzing device comprises a base 1 and a cover 2 and is formed with an introducing chamber 3 and a plurality of microchannels 4.

The base 1 is made of a transparent resin material such as polystyrene (PS), polymethyl methacrylate (PMMA) or polydimethylsiloxane (PDMS), and is in the shape of a disc. The base 1 is formed with indentations that constitute the introducing chamber 3 and the plurality of microchannels 4. The cover 2 is affixed to the base 1. The cover is in the form of a circular film or disc made of a transparent resin material such as polyethylene terephthalate (PET), polystyrene (PS), polymethyl methacrylate (PMMA) or polydimethylsiloxane (PDMS).

The introducing chamber 3 is a site for introducing the specimen S such as blood using a dropper and the like, and is made of a through-hole formed in the cover 2 and a circular indentation formed in the base 1. A separating film (not shown) is provided in the introducing chamber 3. This separating film is interposed, for example, between the base 1 and the cover 2 to separate blood cell components in the blood. A porous substance such as a paper-like material, foam, woven fabric, non-woven fabric, knitted fabric, membrane filter, glass filter or gel-like material can be used for the separating film.

Figure 3:
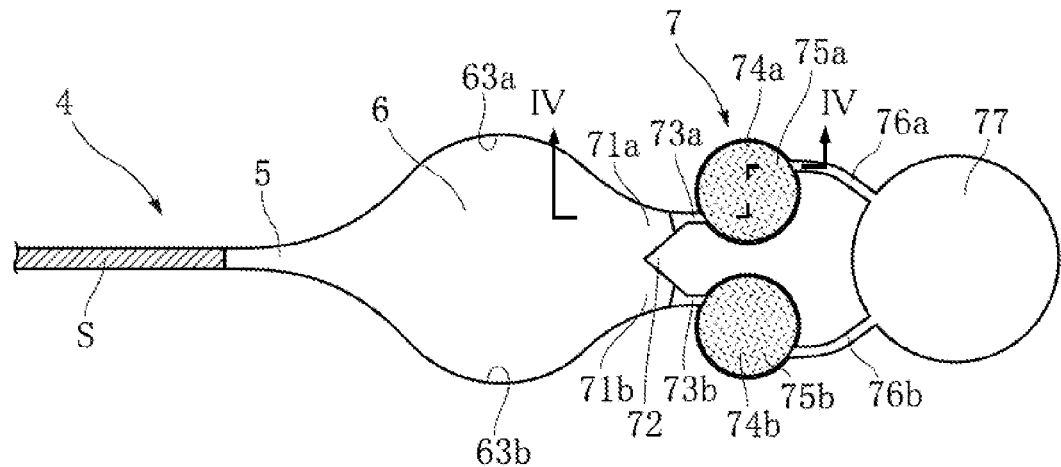
FIG. 3 is a plan view showing the principal parts of an example of a microchannel according to the present invention.

The plurality of microchannels 4 are for transporting the specimen S introduced from the introducing chamber 3 by capillary phenomenon, and a portion thereof is used as the location of analyses using an optical technique. In the present embodiment, the plurality of microchannels 4 extends radially from the introducing chamber 3. As shown in FIG. 3, each of the plurality of microchannels 4 includes an inflow opening 5, an analysis chamber 6 and a discharge portion 7.

The inflow opening 5 is a site where the specimen S that has been introduced into the introducing chamber 3 flows into the analysis chamber 6. In the present embodiment, the width of the inflow opening 5 is about 0.1 mm and the depth is about 0.1 mm.

Figure 4:
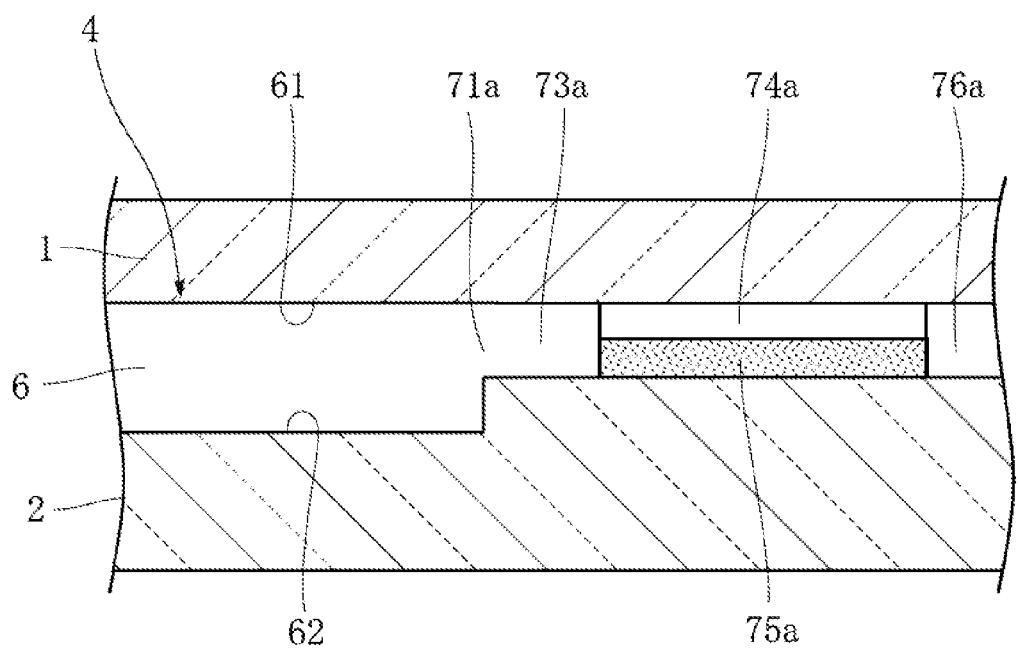
FIG. 4 is a sectional view showing principal parts taken along line IV-IV in FIG. 3.

The analysis chamber 6 is a site for carrying out analyses on the specimen S using an optical technique. The analysis chamber is circular, for example, and has a cross-sectional area which is larger than that of the portions located in front and behind thereof in the direction of flow. The analysis chamber 6 is an example of an enlarged portion defined in the present embodiment. As shown in FIGS. 3 and 4, the analysis chamber 6 is defined by a top surface 61, a bottom surface 62 and a pair of side surfaces 63a and 63b. The top surface 61 and the bottom surface 62 face each other, with a space therebetween, in the vertical direction of FIG. 4 that is perpendicular to the direction of flow. The paired side surfaces 63a and 63b face each other, with a space therebetween, in the width direction that is perpendicular to the vertical direction. In the present embodiment, the distance between the top surface 61 and the bottom surface 62, namely the depth of the analysis chamber 6, is about 0.1 mm. The radius of curvature of the pair of side surfaces 63a and 63b is about 0.6 mm, and from this, the approximate diameter of the analysis chamber 6 is about 1.2 mm.

In the present embodiment, the analysis chamber 6 is coated with a reagent (not shown). This reagent is in the form of a dry solid that dissolves when the specimen S is supplied, and becomes colored as a result of reacting with a specific component in the specimen S. A plurality of types of reagents having different components or compositions, for example, is provided in the analyzing device A so as to enable measurement of a plurality of parameters. However, it is not always necessary to provide the reagents in all of the analysis chambers 6, and coating of the reagent may be omitted for the analysis chambers 6 that are used, for example, to correct for the effects of the color of the specimen itself. In addition, suitable locations other than the analysis chamber 6 may also be coated with a reagent.

The discharge portion 7 is a site where the specimen S is discharged from the analysis chamber 6. The discharge portion includes a pair of discharge openings 71a and 71b, a separating portion 72, a pair of connecting channels 73a and 73b, a pair of retaining portions 74a and 74b, a pair of connecting channels 76a and 76b, and an open chamber 77. The paired discharge openings 71a and 71b are arranged side by side so as to be opposite to each other with respect to the inflow opening 5 as viewed in the direction of flow. The discharge opening 71a is connected to the side surface 63a, while the discharge opening 71b is connected to the side surface 63b. The separating portion 72 demarcates the pair of discharge openings 71a and 71b, and is tapered towards the upstream side in the direction of flow. The pair of connecting channels 73a and 73b are respectively connected to the pair of discharge openings 71a and 71b, and the width thereof is, for example, about 0.05 mm while the depth thereof is about 0.05 mm.

The pair of retaining portions 74a and 74b are circular portions for retaining the discharged specimen S, and are respectively connected to the pair of connecting channels 73a and 73b. In the present embodiment, swelling members 75a and 75b are respectively provided in the retaining portions 74a and 74b. The swelling members 75a and 75b are made of a material in which the volume thereof swells by several to several hundred times as a result of absorbing the specimen S. Examples of such materials that may be used include Aquacork (Sumitomo Seika Chemicals), Wonder-Gel (Kao), Sanwet (Sanyo Chemical Industries) and Aqua Reserve GP (Nippon Synthetic Chemical Industry). The swelling members 75a and 75b are applied to a thickness so as to leave a space in the upper portions of the retaining portions 74a and 74b. The pair of retaining portions 74a and 74b are connected to the open chamber 77 via a pair of connecting channels 76a and 76b. The open chamber 77 is open to the atmosphere via a pathway not shown.

Next, liquid transport in the microchannels 4 is described with reference to FIGS. 5 to 11.

As shown in FIG. 5, the specimen S introduced from the introducing chamber 3 flows through the inflow opening 5 into the analysis chamber 6 by capillary phenomenon. The specimen S that has flowed in has a tendency to progress along the pair of side surfaces 63a and 63b. This is because the portion in the vicinity of each of the side surfaces 63a and 64b comprises a space surrounded on three sides by the top surface 61, the bottom surface 62 and the side surface 63a or 63b. The capillary force of such a space acts more strongly in comparison with a space surrounded on two sides only by the top surface 61 and the bottom surface 62 as in, for example, the central portion of the analysis chamber 6. Consequently, the specimen S proceeds more strongly.

However, it is rare for the side surface 63a and the side surface 63b to be completely identical, and the side surfaces have various differences in nearly all cases. For example, the boundary portion between the side surfaces 63a and 63b and the top surface 61 or the bottom surface 62 is formed to have an extremely minute round shape having a prescribed radius of curvature. Since there are limitations on the processing accuracy of such a boundary portion, a slight amount of error occurs in the round shape. Alternatively, in the case of carrying out surface treatment on e.g. the top surface 61 and bottom surface 62 to make capillary force uniform, variations occur in this processing as well depending on the particular location. In such circumstances, a considerable difference ends up occurring between the speed at which the specimen S proceeds along the side surface 63a and the speed at which the specimen S proceeds along the side surface 63b. In the present embodiment, the speed at which the specimen S proceeds along the side surface 63a is assumed to be relatively fast as shown in FIG. 6. In such a case, as shown in FIG. 7, the specimen S proceeds along the side surface 63a while hardly proceeding at all along the side surface 63b.

Figure 8:
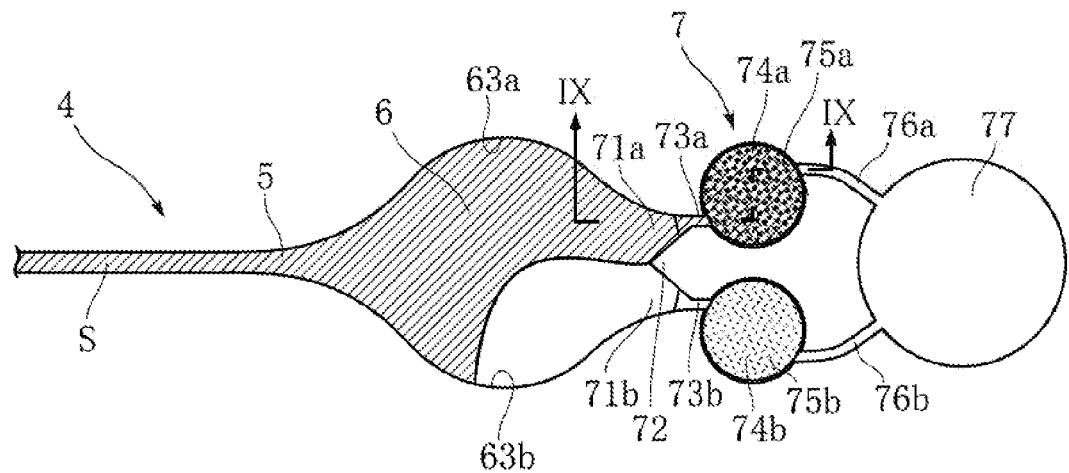
FIG. 8 is a plan view of principal parts depicting liquid transport in the microchannel shown in FIG. 3.

As shown in FIG. 8, as the specimen S proceeds further along the side surface 63a, the specimen S reaches the discharge opening 71a. At this time, the specimen S attempts to also proceed from the discharge opening 71a to the discharge opening 71b. However, since the apex of the separating portion 72 constitutes a sharp angle, the apex demonstrates a considerably large resistance force on the specimen S when it attempts to cross it. Consequently, the specimen S does not proceed to the discharge opening 71b by crossing the separating portion 72. Thus, the specimen S proceeds from the discharge opening 71a to the connecting channel 73a. At this time as well, the specimen S hardly proceeds at all along the side surface 63b.

Figure 9:
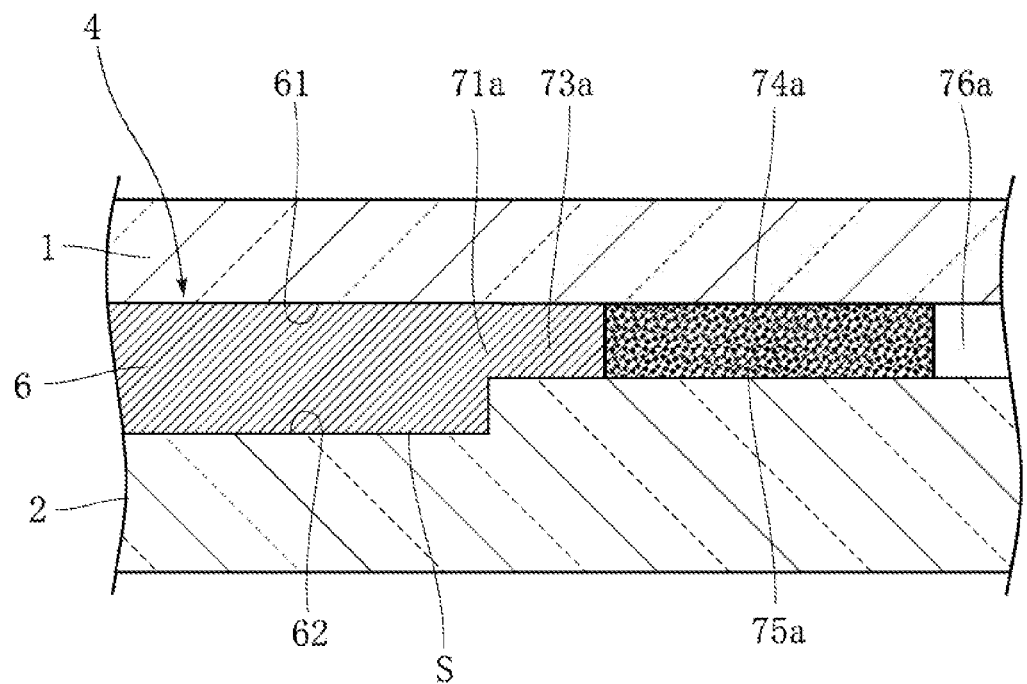
FIG. 9 is a sectional view showing principal parts taken along line IX-IX in FIG. 8.
Figure 10:
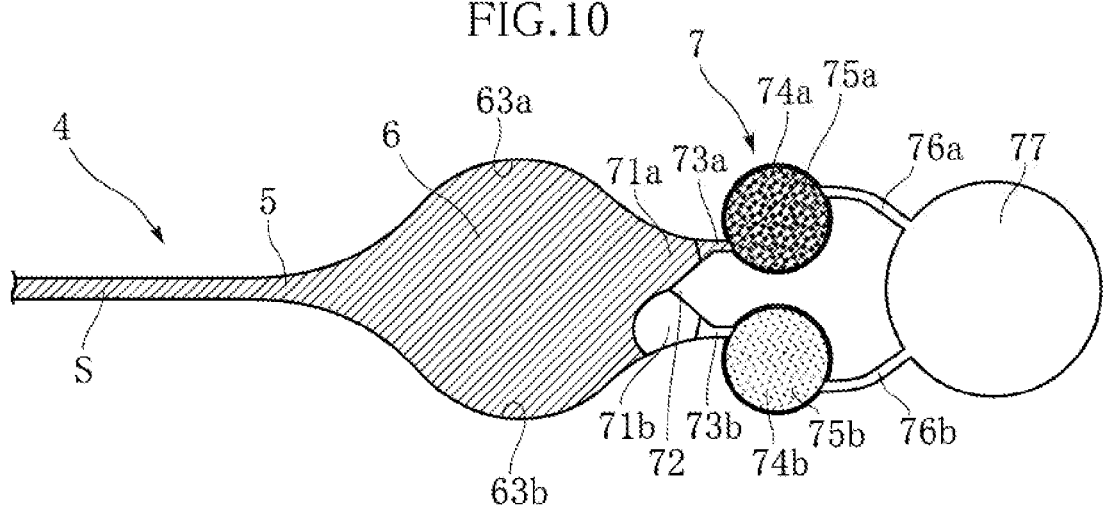
FIG. 10 is a plan view of principal parts depicting liquid transport in the microchannel shown in FIG. 3.
Figure 11:
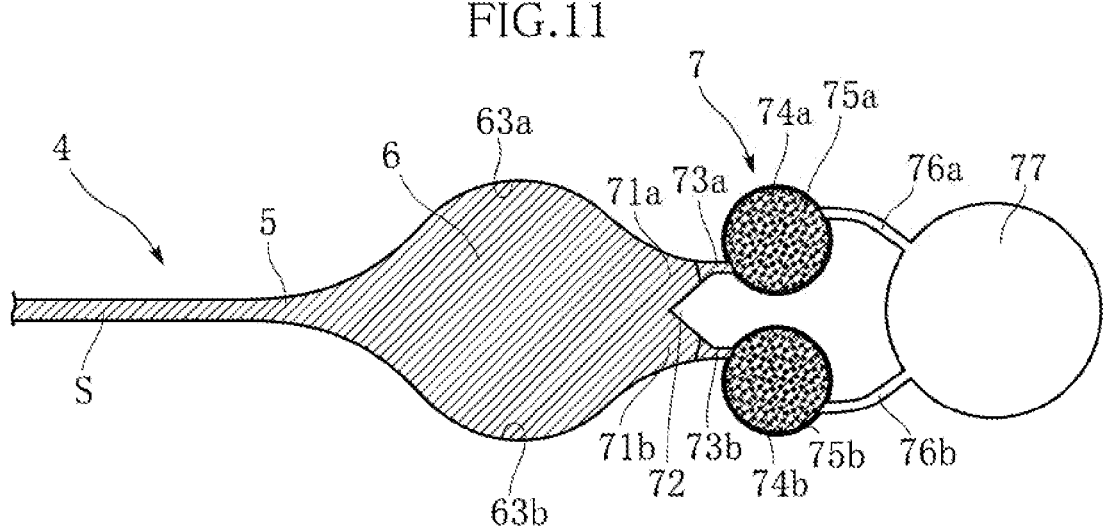
FIG. 11 is a plan view of principal parts depicting liquid transport in the microchannel shown in FIG. 3.

When the specimen S goes beyond the connecting channel 73a and reaches the retaining portion 74a, the specimen S is absorbed by the swelling member 75a. When this happens, the swelling member 75a that has become swollen completely blocks the retaining portion 74a as shown in FIG. 9. As a result, the force that causes the specimen S to proceed through the discharge opening 71a, the connecting channel 73a and the retaining portion 74a no longer acts on the specimen S. Consequently, as shown in FIG. 10, the force that causes the specimen S to move towards the discharge opening 71b, the connecting channel 73b and the retaining portion 74b acts on the specimen S. The specimen S then proceeds along the side surface 63b and reaches the discharge opening 71b as shown in FIG. 11. When the specimen S reaches the retaining portion 74b via the connecting channel 73b, the retaining portion 74b is blocked by swelling of the swelling member 75b. As a result of the above, transport of the specimen S in the microchannel 4 shown ends. Subsequently, analysis is carried out by an optical technique by radiating light from the light emitting module 81 onto the analysis chamber 6 that is filled with the specimen S.

Next, the advantages of the analyzing device A and the microchannels 4 are described.

According to the present embodiment, the specimen S that has flowed into the analysis chamber 6 is discharged from both of the paired discharge openings 71a and 71b. Consequently, even if the specimen S reaches either the discharge opening 71a or 71b first, the remaining specimen S and air present in the analysis chamber 6 can be discharged from the other discharge opening 71a or 71b. Thus, a large air bubble can be prevented from remaining in the analysis chamber 6, thereby enabling analysis by an optical technique to be suitably carried out.

The specimen S easily proceeds along the pair of side surfaces 63a and 63b where capillary force acts more strongly. Since the pair of discharge openings 71a and 71b are connected to these side surfaces 63a and 63b, the specimen S that has proceeded thereto can be reliably discharged from the discharge openings 71a and 71b. In addition, the specimen S that has proceeded to either of the pair of discharge openings 71a and 71b is stopped up by the separating portion 72. Consequently, there is little risk of both the discharge openings 71a and 71b being blocked by the specimen S that has proceeded along either of the pair of side surfaces 63a and 63b. This is suitable for avoiding the retention of an air bubble in the analysis chamber 6.

The pair of retaining portions 74a and 74b are completely blocked by the swelling members 75a and 75b when the specimen S flows therein. Consequently, the specimen S that has been discharged from one of the paired discharge openings 71a and 71b can be prevented from flowing back into the analysis chamber 6 from the other one of the paired discharge openings 71a and 71b. This is suitable for preventing the retention of an air bubble in the analysis chamber 6. Furthermore, even if the swelling members 75a and 75b are not provided unlike the present embodiment, a considerable amount of specimens can still be retained in the retaining portions 74a and 74b. Consequently, the backflow of the specimen S from one of the paired discharge openings 71a and 71b into the other discharge opening can be delayed for a considerable amount of time, and the retention of an air bubble in the analysis chamber can also be avoided in this manner as well.

Figure 12:
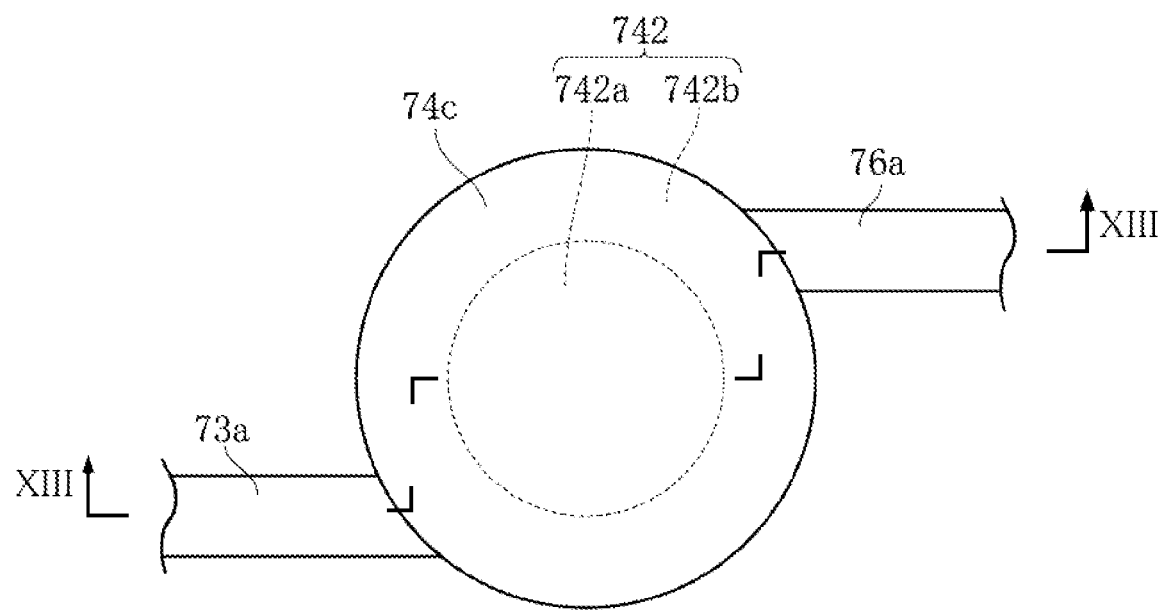
FIG. 12 is a plan view showing the principal parts of another example of a retaining portion.
Figure 13:
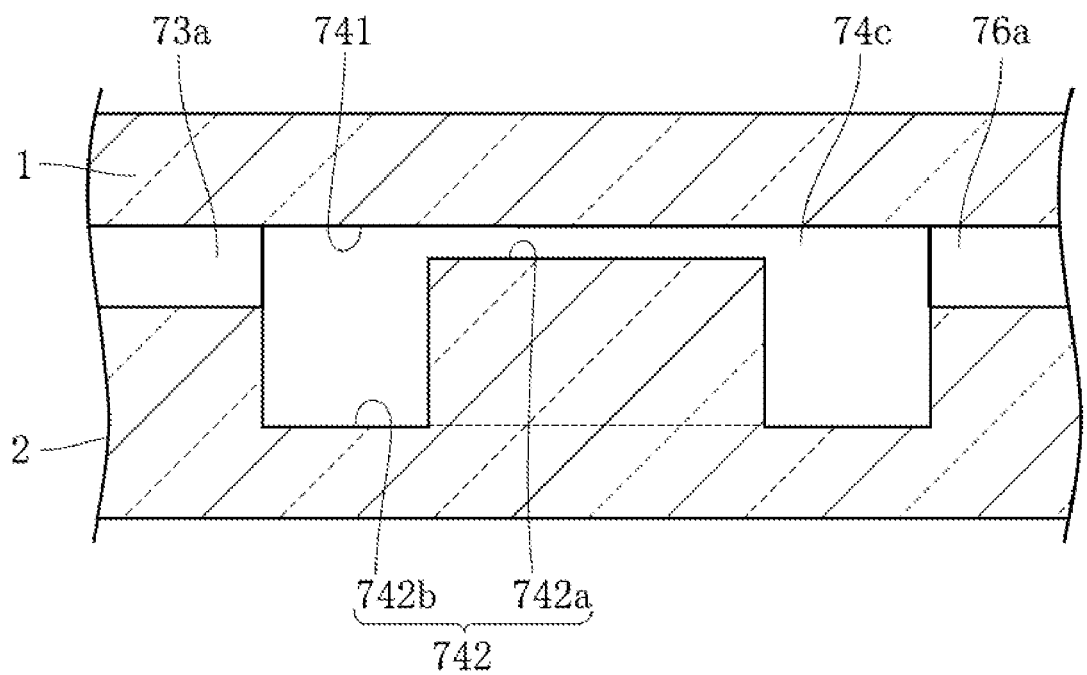
FIG. 13 is a sectional view showing principal parts taken along line XIII-XIII in FIG. 12.

FIGS. 12 and 13 show another example of a retaining portion according to the present invention. The retaining portion 74c shown in the figure has a circular shape when viewed in plan, and as shown in FIG. 13, has a top surface 741 and a bottom surface 742. The top surface 741 is a flat surface that does not have a level difference, and flush with the upper surfaces of connecting channels 73a and 76a. The bottom surface 742 as a whole faces the top surface 741 with a space therebetween, and is made up of an island portion 742a and a surrounding portion 742b. As shown in FIG. 12, the island portion 742a is a portion that is located towards the center of the bottom surface 742, and in the present embodiment, has a circular shape when viewed in plan. The surrounding portion 742b surrounds the island portion 742a when viewed in plan, and in the present embodiment, has a doughnut shape when viewed in plan. As shown in FIG. 13, the island portion 742a is relatively close to the top surface 741. On the other hand, the surrounding portion 742b is farther away from the top surface 741 than the island portion 742a is.

Figure 14:
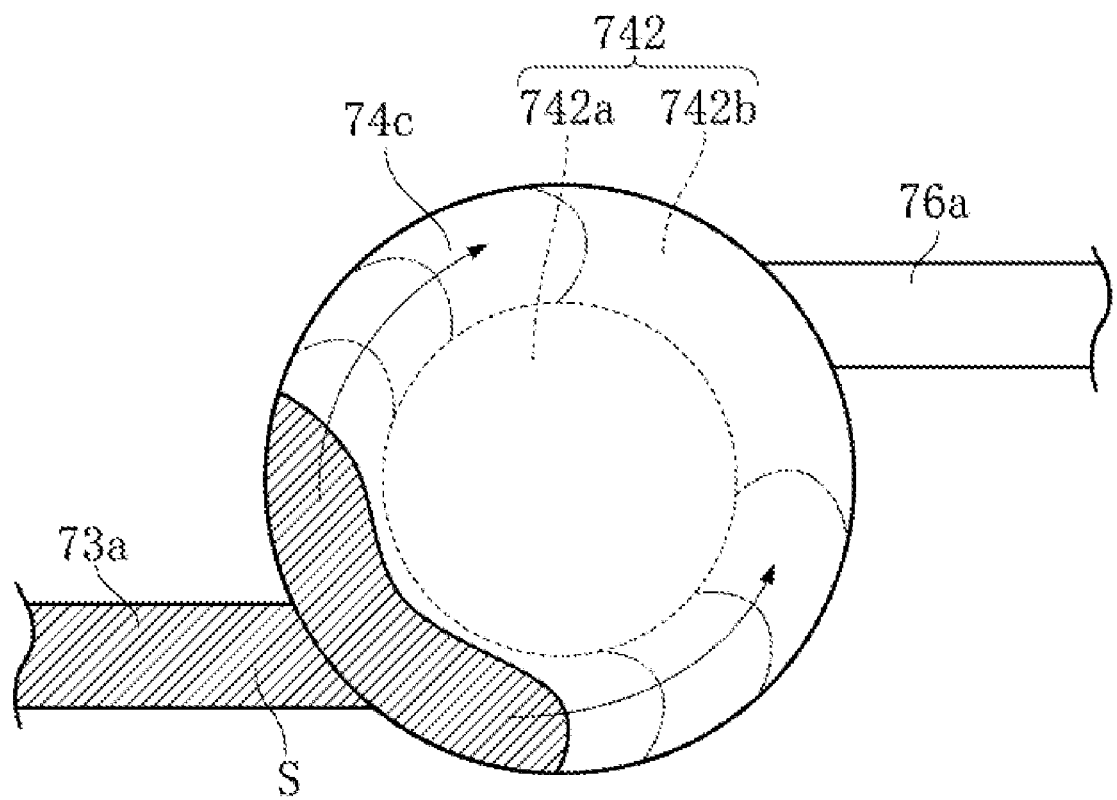
FIG. 14 is a plan view of principal parts depicting the flow of a liquid in the retaining portion shown in FIG. 12.

As shown in FIG. 14, when the specimen S flows into the retaining portion 74c from the connecting channel 73a, the specimen S is retained between the surrounding portion 742b and the top surface 741, and does not enter the space between the island portion 742a and the top surface 741. As inflow of the specimen S proceeds further, the specimen S proceeds within the retaining portion 74c while being divided into two flows following the shape of the surrounding portion 742b. When air within the microchannel 4 attempts to flow with the inflow of the specimen S, the air is discharged to the connecting channel 76a after passing between the island portion 742a and the top surface 741. When the entire surrounding portion 742b is covered with the specimen S, the specimen S subsequently flows out to the connecting channel 76a. With this arrangement as well, backflow of the specimen S from one of the paired discharge openings 71a and 71b as shown in FIG. 3 to the other discharge opening can be delayed for a considerable amount of time, thereby making it possible to avoid retention of air bubbles.

Figure 15:
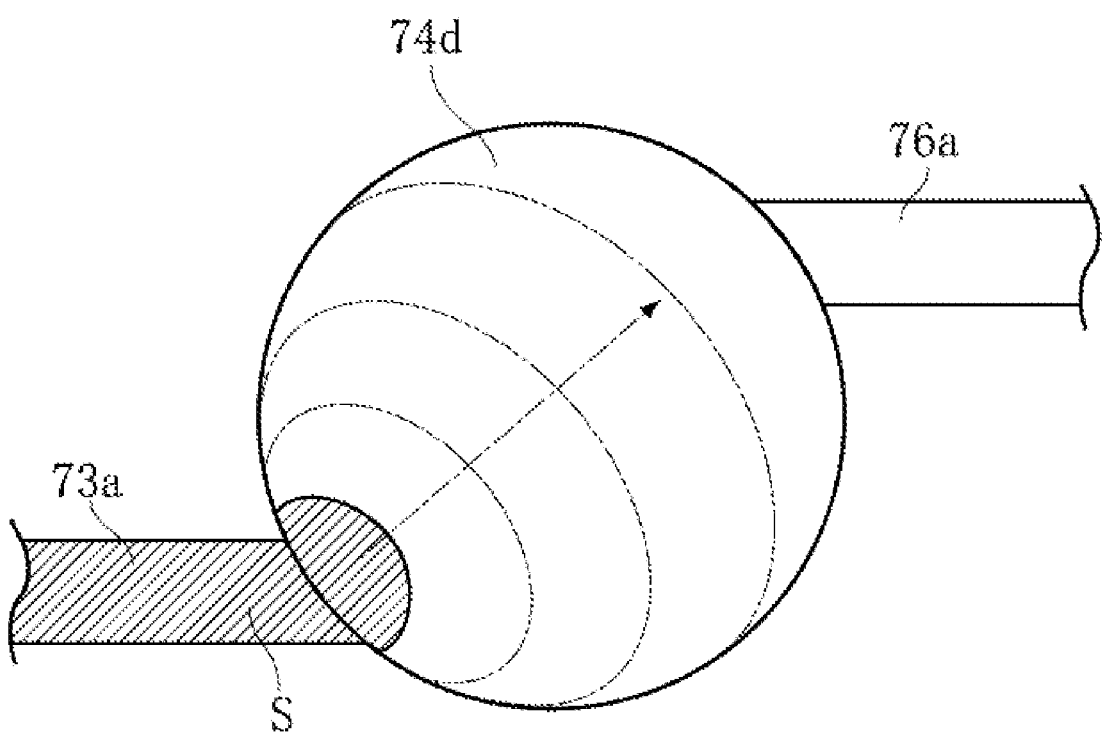
FIG. 15 is a plan view of the principal parts of still another example of a retaining portion.

FIG. 15 shows still another example of a retaining portion according to the present invention. The retaining portion 74d shown in the figure has a hydrophobic region in which the inner surface thereof has been subjected to hydrophobic treatment, and in the present embodiment, the top surface and the bottom surface constitute this hydrophobic region. In this case, resistance force by which the progression of the specimen is impaired is imparted by this hydrophobic region to the specimen S which is flown from the connecting channel 73a. As a result, the retaining portion 74b is able to delay outflow of the specimen S to the connecting channel 76a located on the downstream side thereof. With this arrangement as well, backflow of the specimen S from one of the paired discharge openings 71a and 71b as shown in FIG. 3 to the other discharge opening can be delayed for a considerable amount of time, thereby making it possible to avoid retention of air bubbles.

Figure 16:
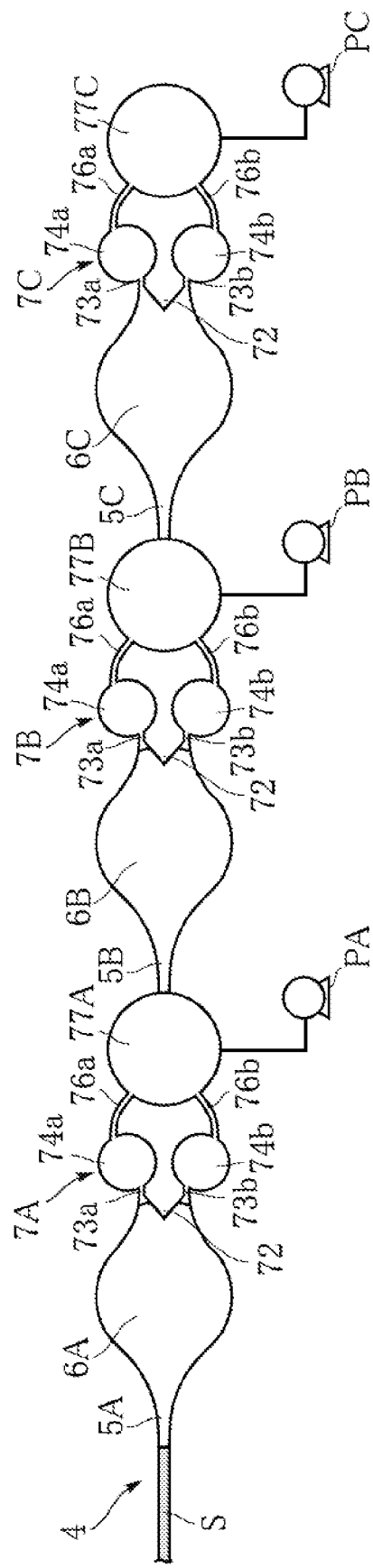
FIG. 16 is a plan view of the principal parts of another example of a microchannel according to the present invention.
Figure 17:
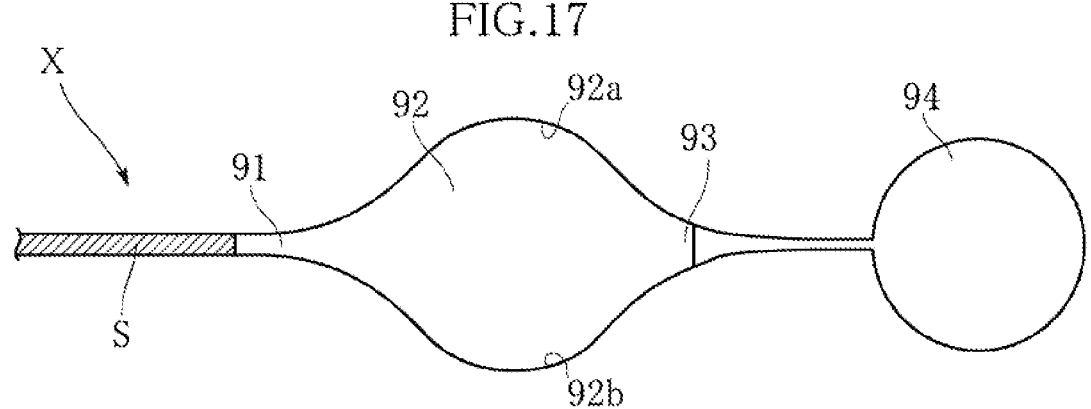
FIG. 17 is a plan view showing the principal parts of an example of a conventional microchannel.
Figure 18:
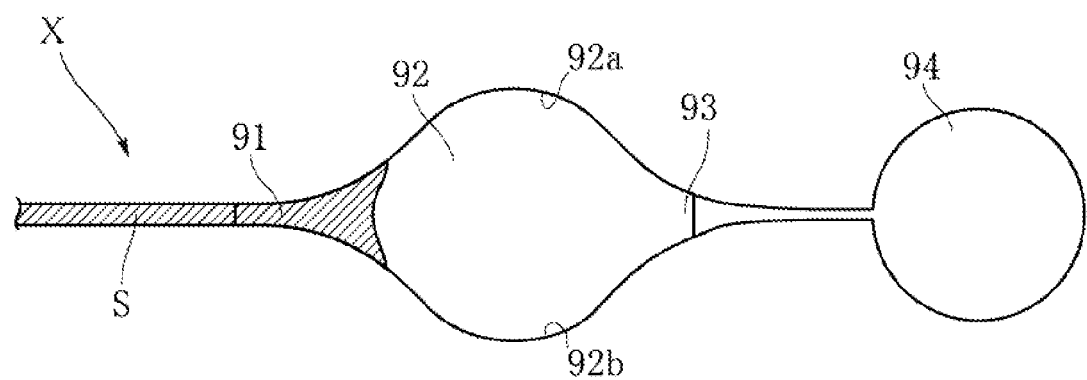
FIG. 18 is a plan view of principal parts showing liquid transport in the microchannel shown in FIG. 12.
Figure 19:
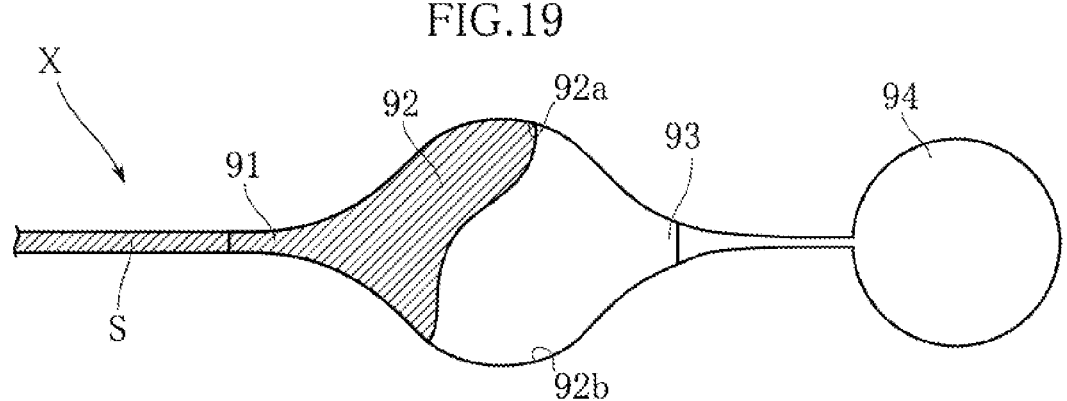
FIG. 19 is a plan view of principal parts showing liquid transport in the microchannel shown in FIG. 12; and, FIG. 20 is a plan view of principal parts showing liquid transport in the microchannel shown in FIG. 12.
Figure 20:
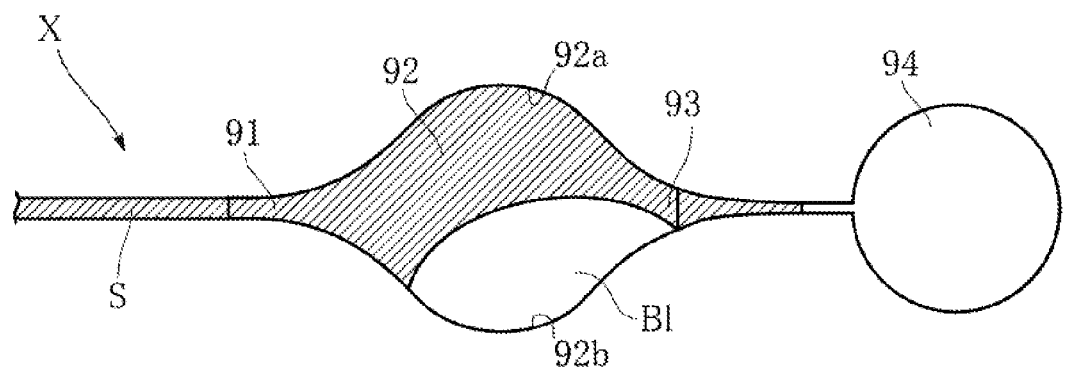

FIG. 16 shows another example of a microchannel according to the present invention. The microchannel 4 shown in the figure includes three analysis chambers 6A, 6B and 6C connected to each other. The following provides an explanation of liquid transport using this microchannel 4. First, the specimen S is transported from the inflow opening 5A to the retaining portions 74a and 74b of a discharge portion 7A via the analysis chamber 6A using the same method as the liquid transport explained with reference to FIGS. 5 to 11. In the analysis chamber 6A, the specimen S reacts with, for example, a reagent applied in advance to the chamber. The retaining portions 74a and 74b of the present embodiment comprise relatively large-volume liquid tanks which do not contain the above-described swelling members 75a and 75b. The above-mentioned retaining portions 74c or 74d may also be employed instead of the retaining portions 74a and 74b. In the present embodiment, a pressure reducing pump PA as pressure reducing means is connected to the open chamber 77A of the discharge portion 7A. After transport to the retaining portions 74a and 74b has been completed, the specimen S flows into the open chamber 77A when the internal pressure of the open chamber 77A is reduced by the pressure reducing pump PA.

Next, an open chamber 77B of the discharge portion 7B on the downstream side of the analysis chamber 6B is opened to the atmosphere. When this happens, the specimen S is transported from the inflow opening 5B to the retaining portions 74a and 74b of the discharge portion 7B via the analysis chamber 6B in the same manner as the liquid transport explained with reference to FIGS. 5 to 11. In the analysis chamber 6B, the specimen is allowed to react, for example, with a different reagent from the reagent of the analysis chamber 6A. Alternatively, in the case where the analysis chamber 6B is of a configuration in which a reagent is not applied, the analysis chamber 6B may be used to correct for the effects of the color of the specimen itself. A pressure reducing pump PB is connected to the open chamber 77B. The specimen S flows into the open chamber 77B when the internal pressure of the open chamber 77B is reduced by the pressure reducing pump PB.

Moreover, when an open chamber 77C of a discharge portion 7C on the downstream side of the analysis chamber 6C is opened to the atmosphere, the specimen S is sent from the inflow opening 5C to the retaining portions 74a and 74b of the discharge portion 7C via the analysis chamber 6C. In the analysis chamber 6C, the specimen S is allowed to react, for example, with another different type of reagent. A pressure reducing pump PC is connected to the open chamber 77C. The specimen S flows into the open chamber 77C when the internal pressure of the open chamber 77C is reduced by the pressure reducing pump PC.

Thus, according to the present embodiment, processing in the plurality of analysis chambers 6A, 6B and 6C can be carried out consecutively. This is suitable for carrying out different types of tests on the same specimen in a short period of time. In addition, inflow of the specimen S into the open chamber 77C means that the specimen is ready to be further transported downstream from this chamber. Thus, different tests can also be carried out by adding different analysis chambers to the analysis chambers 6A, 6B and 6C and transporting the specimen S thereto.

The microchannel and analyzing device according to the present invention are not limited to the above-described embodiments. The specific structure of each portion of the microchannel and analyzing device according to the present invention may be varied in design in various ways.

The analysis chamber 6 corresponding to an enlarged portion defined in the present invention is not limited to that having a circular shape, but rather is only required to have a shape that is able to suitably realize analysis by an optical technique while allowing transport of the specimen S by capillary phenomenon. Although the pair of discharge openings 71a and 71b is preferably demarcated by the separating portion 72, the present invention is not limited thereto. Although the pair of retaining portions 74a and 74b and the swelling members 75a and 75b provided therein are preferable for the purpose of preventing backflow of the specimen S, a configuration not provided therewith may also be employed provided that a configuration that makes it difficult for the specimen S to flow back through the microchannel 4 is provided on the downstream side of the discharge portion 7.

The analyzing device A is an example of a device which carries out liquid transport using the microchannel 4, and may be a device which carries out analysis other than the analysis using an optical technique, for example. In addition, the liquid used for the specimen S is naturally not limited to blood. Although the microchannel according to the present invention is preferably used to analyze minute amounts of blood, it is not limited thereto, but rather can also be used in various applications in which a liquid is to be transported through an enlarged portion. Moreover, the microchannel according to the present invention is not limited to that which uses capillary phenomenon as the driving force of liquid transport, but rather a structure may also be employed in which a liquid is transported by a relatively small pressure difference generated in front of and behind the microchannel in the direction of flow. This structure can also be expected to demonstrate the effect of inhibiting an air bubble from remaining in the enlarged portion, thereby enabling smooth liquid transport.

The invention claimed is:

1. A microchannel for transporting a liquid, comprising:
an inflow portion located on an upstream side in a direction of flow;
a discharge portion located on a downstream side in the direction of flow; and
an enlarged portion located between the inflow portion and the discharge portion and having a cross-sectional area larger than those of the inflow portion and the discharge portion;
wherein the discharge portion includes a pair of discharge openings located opposite to each other with respect to the inflow portion as viewed in the direction of flow,
wherein the discharge portion further includes a retaining portion that is connected to at least one of the discharge openings on the downstream side in the direction of flow and has a cross-sectional area larger than that of the discharge opening,
wherein the retaining portion is provided with a swelling member that inhibits outflow of the liquid from the retaining portion to the downstream side by swelling upon absorbing the liquid.

2. The microchannel according to claim 1, wherein the liquid is transported using capillary phenomenon.

3. The microchannel according to claim 1, wherein the discharge portion further includes a separating portion located between the discharge openings and tapered towards the upstream side in the direction of flow.

4. The microchannel according to claim 1, further comprising:
an additional enlarged portion located on the downstream side of the retaining portion in the direction of flow;
an additional inflow portion for guiding the liquid from the retaining portion to the additional enlarged portion; and
an additional discharge portion into which the liquid from the additional enlarged portion is discharged and includes a pair of additional discharge openings located opposite to each other with respect to the additional inflow portion as viewed in the direction of flow.

5. The microchannel according to claim 4, wherein an open chamber that can be open to the atmosphere is provided between the retaining portion and the additional inflow portion.

6. The microchannel according to claim 5, wherein the open chamber is connected to a pressure reducer capable of reducing pressure within the open chamber.

7. An analyzing device, comprising the microchannel as set forth in claim 1, wherein the enlarged portion is used as an analysis field.

* * * * *